(12) United States Patent
Higuchi et al.

(10) Patent No.: US 7,910,061 B2
(45) Date of Patent: Mar. 22, 2011

(54) COLORIMETRIC ABSORBANCE MEASUREMENT APPARATUS

(75) Inventors: Yasuhiro Higuchi, Nishinomiya (JP); Yoshinori Fujiwara, Nishinomiya (JP)

(73) Assignee: Furuno Electric Company, Limited, Nishinomiya-shi (JP)

( * ) Notice: Subject to any disclaimer, the term of this patent is extended or adjusted under 35 U.S.C. 154(b) by 732 days.

(21) Appl. No.: 10/247,543

(22) Filed: Sep. 20, 2002

(65) Prior Publication Data
US 2003/0072680 A1    Apr. 17, 2003

(30) Foreign Application Priority Data

Sep. 20, 2001    (JP) ................................ 2001-286009

(51) Int. Cl.
*G01N 21/00*    (2006.01)
*G01N 35/02*    (2006.01)
*G01N 31/00*    (2006.01)
*G01N 21/75*    (2006.01)

(52) U.S. Cl. ................. 422/64; 422/63; 422/65; 436/47; 436/164

(58) Field of Classification Search ............... 422/82.05, 422/82.09; 356/414, 418
See application file for complete search history.

(56) References Cited

U.S. PATENT DOCUMENTS

| | | | | |
|---|---|---|---|---|
| 3,655,288 A | * | 4/1972 | Lieberman et al. | 356/315 |
| 3,861,788 A | * | 1/1975 | Webster | 359/889 |
| 3,982,130 A | * | 9/1976 | Trumble | 250/373 |
| 4,134,678 A | * | 1/1979 | Brown et al. | 356/39 |
| 4,325,910 A | * | 4/1982 | Jordan | 422/64 |
| 4,629,703 A | * | 12/1986 | Uffenheimer | 436/45 |
| 5,036,198 A | | 7/1991 | Spaeth | |

FOREIGN PATENT DOCUMENTS
EP    0 243 139 A3    10/1987
GB    2105058 A    3/1983

* cited by examiner

*Primary Examiner* — Jill Warden
*Assistant Examiner* — Neil Turk
(74) *Attorney, Agent, or Firm* — Birch, Stewart, Kolasch & Birch, LLP

(57) ABSTRACT

In a colorimetric absorbance measurement apparatus, a filter assembly on which a plurality of filters are arranged in a circular pattern is continuously rotated by a motor at a regular speed based on a motor drive signal fed from a motor drive circuit, each of the filters being characterized by passing only such light components that have wavelengths falling within a range centering on a specific wavelength. The motor drive signal produced by the motor drive circuit is also fed into a timing generator circuit. The timing generator circuit supplies an A/D conversion start signal to an A/D converter in synchronism with the timing at which a selected one of the multiple filters is positioned on the optical axis of a measuring light beam.

12 Claims, 5 Drawing Sheets

COLORIMETRIC ABSORBANCE MEASUREMENT APPARATUS

BACKGROUND OF THE INVENTION

1. Field of the Invention

This invention relates to a calorimetric absorbance measurement apparatus used in a biochemical analyzer.

2. Description of the Prior Art

Measurement of cholesterol levels or other biochemical data using such samples as blood plasma, serum or urine is carried out by using a biochemical analyzer, for example. Generally, this sort of measurement is performed by injecting a sample held in a sample tube and a reagent held in a reagent bottle into a cuvette which is formed of heat-resistant hard glass placed in a reaction vessel to cause a reaction therein, and measuring the absorbance of a reaction fluid to determine the cholesterol level, for instance, from obtained data.

A colorimetric absorbance measurement method is commonly used for measuring the absorbance. In this measurement method, a light source like an incandescent lamp emits light containing multiple wavelengths, a filter passes only such light components that have wavelengths falling within a range centering on a specific wavelength suited to an intended test item, and the light of the specific range of wavelength is passed through the reaction fluid in the cuvette to measure its absorbance. The filter commonly used in the colorimetric absorbance measurement method for taking out the desired wavelengths is a glass filter or an interference filter placed in a light path, for instance. An alternative to this filtering method that has also been commonly used is a grating method which disperses light from a light source into its wavelength components by use of a diffraction grating, for example.

Since the grating method is relatively expensive and makes it difficult to reduce equipment size due to the use of the diffraction grating, for instance, the filtering method has conventionally been used more often than the grating method in small-sized analyzers.

Since the colorimetric absorbance measurement utilizes different wavelengths depending on test items as stated above, it is essential to successively take out wavelengths of several ranges when conducting multiple tests. Whereas the diffraction grating used in the grating method selectively takes out wavelengths of several ranges at the same time, each filter used in the filtering method can take out wavelengths of one range only. Therefore, it is necessary to prepare multiple filters suitable for intended test items when using the filtering method.

As an example of a prior art arrangement, Japanese Laid-open Patent Publication No. 8-68788 discloses an apparatus for automatically measuring the quality, color and turbidity of tap water using the filtering method for calorimetric absorbance measurement, although this apparatus is not used as a biochemical analyzer for measuring samples in multiple cuvettes while sequentially moving them to the optical axis of a measuring light beam. The apparatus of the disclosure is constructed such that light emitted from a light source is passed through a cell containing water to be tested and a filter which transmits light components of wavelengths falling within a range centering on a specific wavelength, and the light components which have passed through the cell and the filter are converted into an electric signal, from which measurement results are calculated and output. In this apparatus, a rotating disklike light-dispersing device provided with at least four filters capable of passing specific wavelengths is caused to rotate and halt in successive steps, and a measurement is made when each filter has come to a halt.

The apparatus disclosed in the aforementioned Patent Publication controllably rotates the disklike light-dispersing device in such a way that the filter suited to the test item is placed in the light path and a measurement of the absorbance is performed when the light-dispersing device is at a halt. This approach, however, has a problem that a relatively long period of time is required for each measurement because the measurement should be made after each filter of the disklike light-dispersing device has been completely halted. More specifically, this approach requires a long measurement time overall and the number of wavelengths at which calorimetric absorbance measurements are performed for individual reaction fluids decreases. If the measurement is carried out before each filter of the disklike light-dispersing device is completely halted to achieve a high efficiency, the reliability of measurement data will deteriorate.

SUMMARY OF THE INVENTION

In view of the foregoing, it is an object of the invention to provide a calorimetric absorbance measurement apparatus which makes it possible to achieve a high measuring efficiency while ensuring highly reliable measurement data.

In a first form of the invention, a calorimetric absorbance measurement apparatus comprises a light source, a cuvette which contains a sample and is held on the optical axis of a measuring light beam during a measurement, a filter assembly on which a plurality of filters are arranged in a circular pattern, each of the filters being characterized by passing only such light components that have wavelengths falling within a range centering on a specific wavelength, a motor for rotating the filter assembly about its central axis, causing the multiple filters to sequentially intersect the optical axis of the light beam, a motor driver for driving the motor such that the filter assembly continuously rotates at a regular speed, a photoelectric converter converting light which has passed through a selected one of the multiple filters and the cuvette into an electric signal, a signal processor for processing an output signal of the photoelectric converter, and a controller for causing the signal processor to perform the signal processing tasks in synchronism with the timing at which the selected one of the multiple filters is positioned on the optical axis of the light beam.

This apparatus performs the signal processing tasks in synchronism with the timing at which the selected one of the multiple filters is positioned on the optical axis of the light beam while causing the filter assembly to continuously rotate at the regular speed and taking calorimetric absorbance measurements. By causing the filter assembly to continuously rotate at the regular speed in this way, the calorimetric absorbance measurement apparatus of the invention solves the aforementioned problem of the prior art that it is impossible to obtain measurements until vibrations caused by halting the filter assembly fade away, thereby enabling achievement of a high measuring efficiency. Furthermore, since the filter assembly is rotated at the regular speed, the reliability of measurement data will not deteriorate due to the vibrations unlike the case of the prior art. Overall, the invention makes it possible to obtain highly reliable measurement data, shorten the period of time required for measurement and increases the number of wavelengths at which calorimetric absorbance measurements are performed within a given time period.

In one feature of the invention, the calorimetric absorbance measurement apparatus comprises a plurality of cuvettes which are conveyed and halted such that the cuvettes are sequentially held on the optical axis of the light beam.

When the apparatus is provided with a plurality of cuvettes as stated above, it is necessary to transfer the cuvette to be subjected to a next measurement to a measuring position upon completing the measurement of the preceding cuvette. Basically, it is preferable to perform a measurement after vibrations of the cuvettes have completely ceased, as is so with vibrations of the filter assembly of the prior art. Since the aforementioned calorimetric absorbance measurement apparatus of the invention provides a high measuring efficiency as stated above, a sufficient time period is allowed to wait until the vibrations caused by halting each cuvette completely fade away. It is therefore possible to prevent deterioration of measuring accuracy caused by the vibrations of the cuvettes. Furthermore, because measurements are successively taken from the multiple cuvettes, it is possible to obtain measurements of different samples one after another in a limited period of time.

Synchronization between the signal processing tasks and the rotation of the filter assembly may be accomplished by the controller using a motor drive signal fed from the motor driver or a control signal transmitted by the controller itself to the motor driver. Alternatively, the colorimetric absorbance measurement apparatus may further comprise an encoder for outputting a rotating speed signal indicating the rotating speed of the motor or the filter assembly, so that the controller can synchronize the signal processing tasks with the rotation of the filter assembly based on this rotating speed signal.

In a second form of the invention, a calorimetric absorbance measurement apparatus comprises a light source, a plurality of cuvettes containing samples, the cuvettes being conveyed and halted such that they are sequentially held on the optical axis of a measuring light beam, a filter assembly on which a plurality of filters are arranged in a circular pattern, each of the filters being characterized by passing only such light components that have wavelengths falling within a range centering on a specific wavelength, a turning device for continuously rotating the filter assembly about its central axis at a specific speed, thereby causing the multiple filters to sequentially intersect the optical axis of the light beam, a photoelectric converter for converting light which has been emitted from the light source and passed through a selected one of the multiple filters and the cuvette positioned on the optical axis of the light beam into an electric signal, a signal processor for processing an output signal of the photoelectric converter, and a controller for synchronizing operation of the photoelectric converter with the timing at which the selected one of the multiple filters is positioned on the optical axis of the light beam.

The colorimetric absorbance measurement apparatus of the second form of the invention confers the same advantages as gained from the apparatus of the first form of the invention as well as from the apparatus of the first form provided with the multiple cuvettes.

In a third form of the invention, a colorimetric absorbance measurement apparatus comprises a light source, a plurality of cuvettes each containing a mixture of a reagent and a sample, which are arranged in a circular form at substantially regular intervals, with each of the cuvettes being conveyed to the optical axis of a measuring light beam, a turning device for continuously rotating said reaction vessels, thereby causing the multiple cuvetts to move to axis of the light beam sequentially, a filter assembly on which a plurality of filters are arranged in a circular pattern, each of the filters passing only such light components that have wavelengths falling within a range centering on a specific wavelength, a turning device for continuously rotating said filter assembly about its central axis at a speed, thereby causing the multiple filters to sequentially intersect the optical axis of the light beam, a photoelectric converter for converting light which has been emitted from said light source and passed through a selected one of the multiple filters and one of the cuvettes on the optical axis of the light beam into an electric signal, a signal processor for processing an output signal of said photoelectric converter, and a motor/sensor control circuit for synchronizing operation of said photoelectric converter with the timing at which the selected one of the multiple filters is on the optical axis of the light beam.

These and other objects, features and advantages of the invention will become more apparent upon reading the following detailed description in conjunction with the accompanying drawings.

DETAILED DESCRIPTION OF THE PREFERRED EMBODIMENTS OF THE INVENTION

Specific embodiments of the invention are now described with reference to the accompanying drawings.

Figure 1:
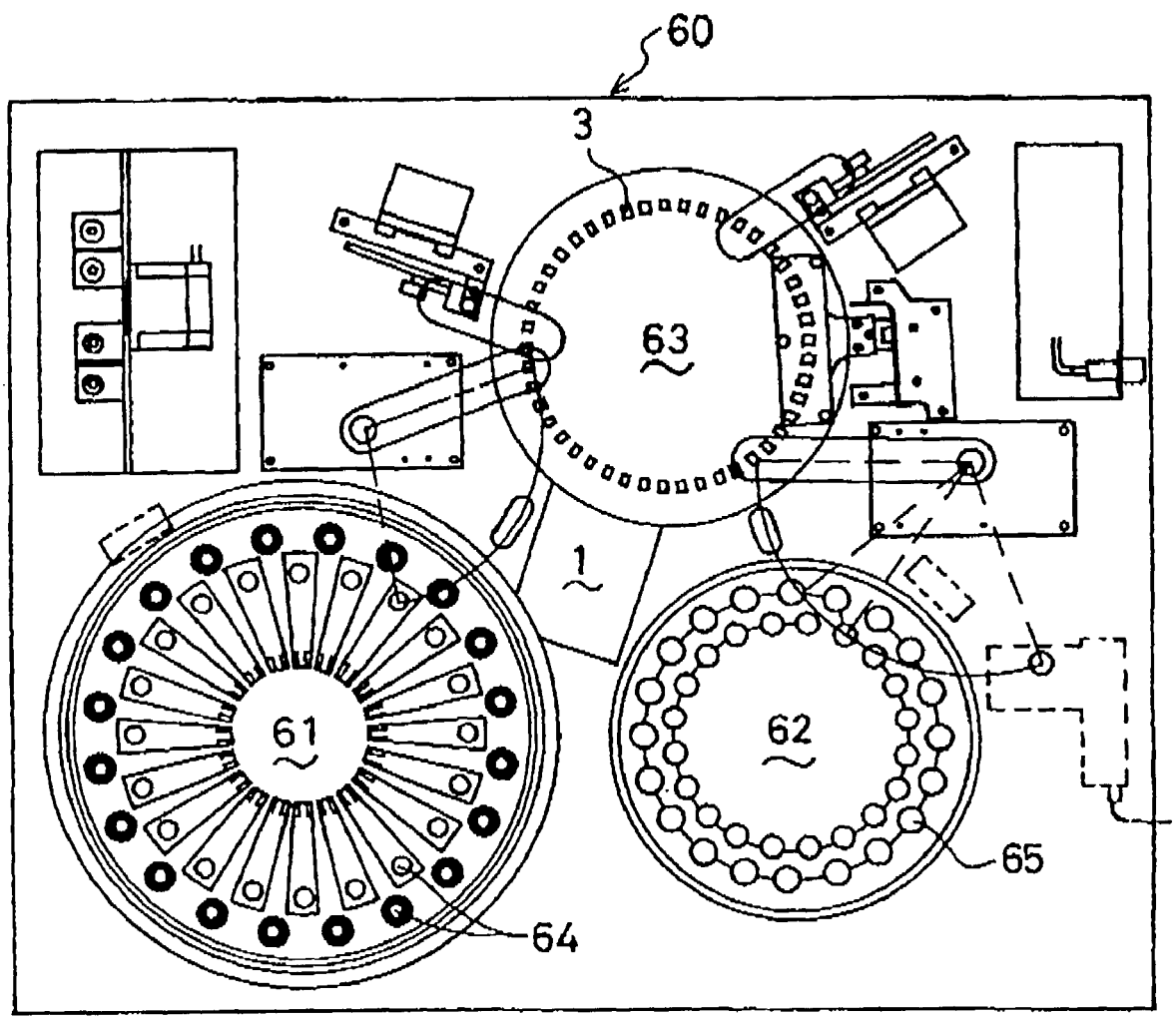
FIG. 1 is a plan view of a biochemical analyzer comprising a calorimetric absorbance measurement apparatus according to a first embodiment of the invention.
Figure 2:
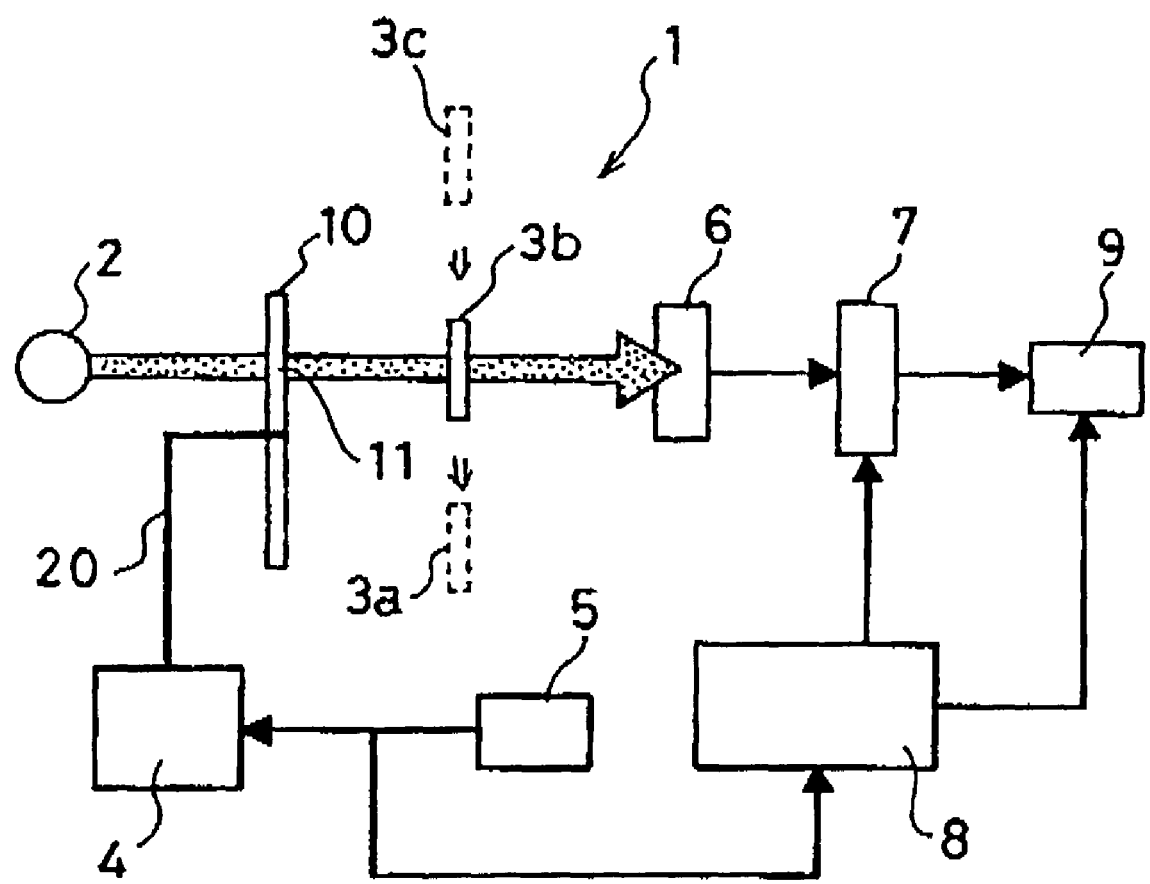
FIG. 2 is a block diagram of the calorimetric absorbance measurement apparatus according to the first embodiment of the invention.
Figure 3:
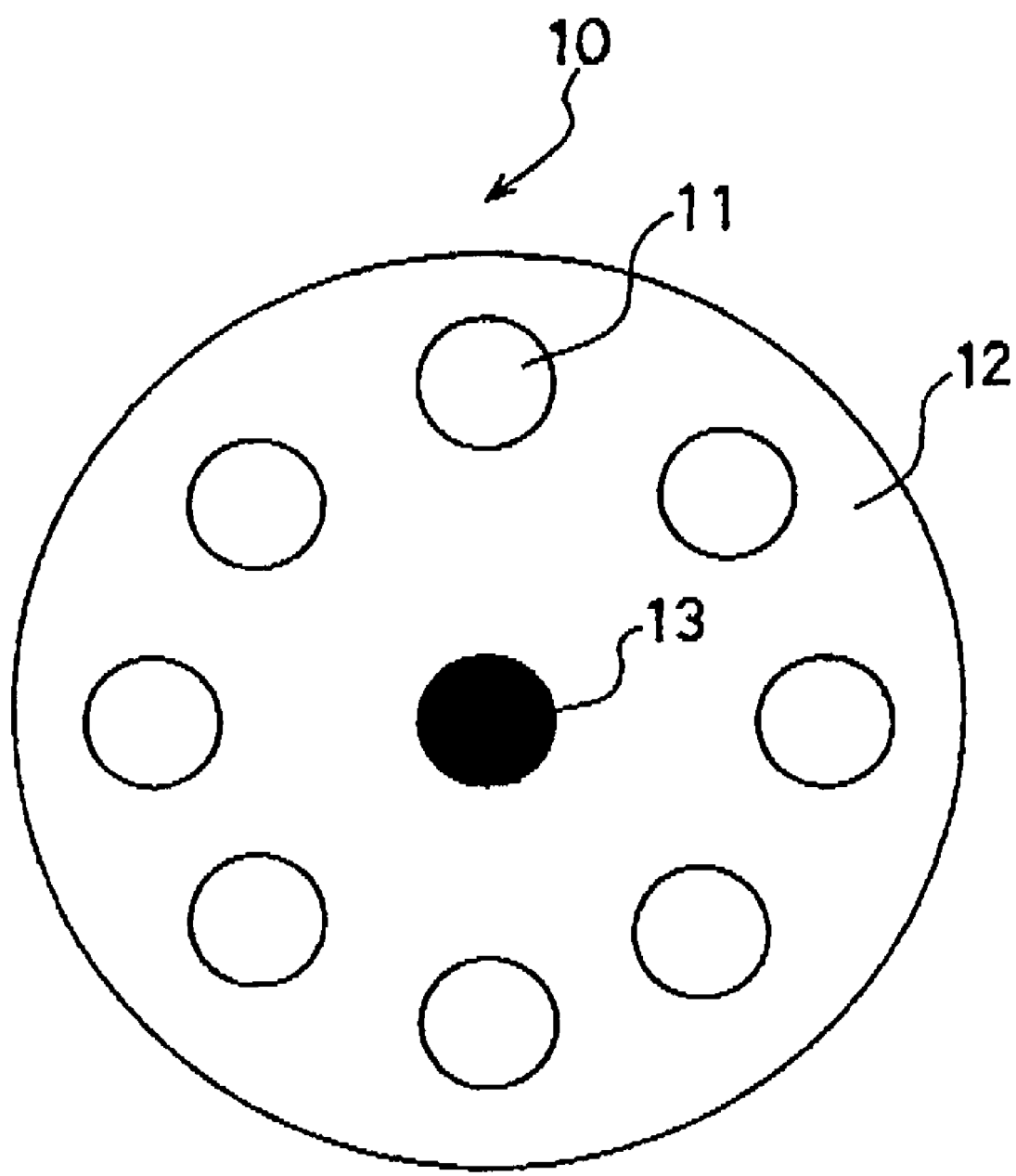
FIG. 3 is a front view of a filter assembly used in the colorimetric absorbance measurement apparatus of FIG. 2.
Figure 4:
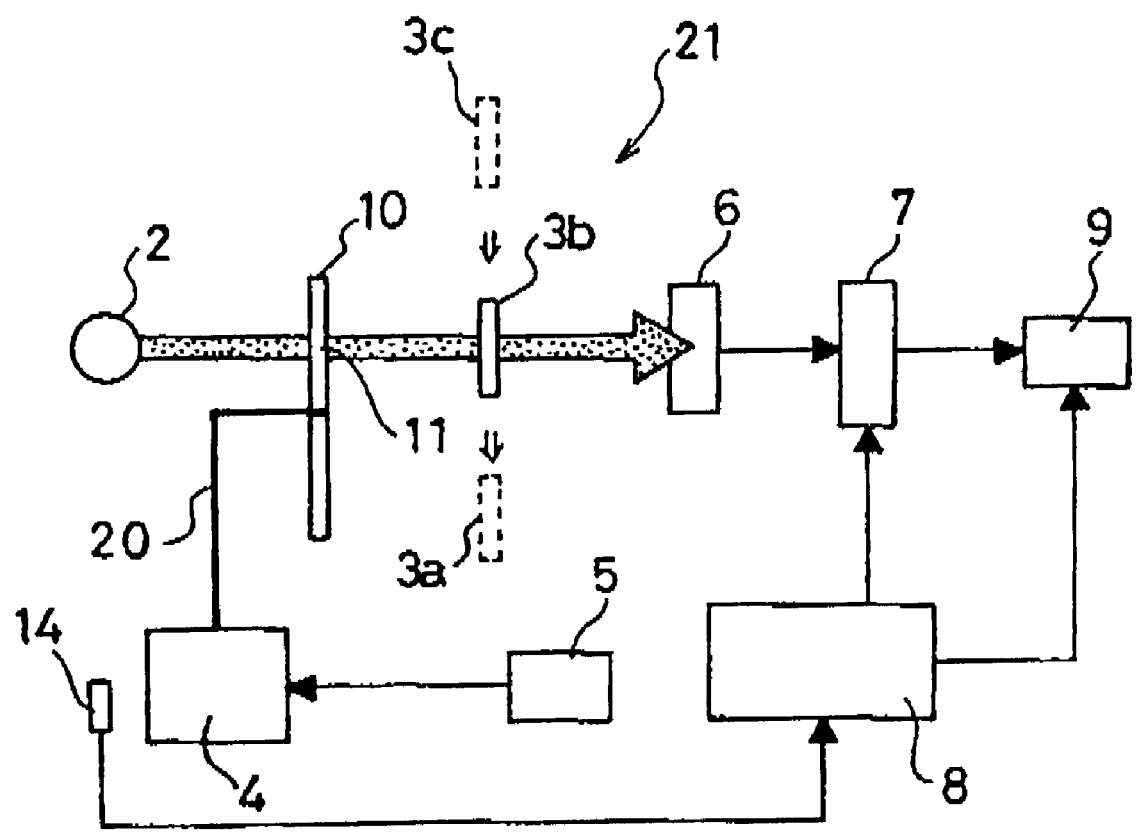
FIG. 4 is a block diagram of a calorimetric absorbance measurement apparatus according to a second embodiment of the invention.

FIG. 1 is a plan view of a biochemical analyzer 60 comprising a colorimetric absorbance measurement apparatus 1 according to a first embodiment of the invention; FIG. 2 is a block diagram of the calorimetric absorbance measurement apparatus 1 according to the first embodiment of the invention; FIG. 3 is a front view of a filter assembly 10 used in the colorimetric absorbance measurement apparatus 1 of FIG. 2; and FIG. 4 is a block diagram of a calorimetric absorbance measurement apparatus 21 according to a second embodiment of the invention.

The construction of the aforementioned biochemical analyzer 60 featuring a compact desktop design shown in FIG. 1 is first described. Used for measuring cholesterol levels or other biochemical data from such samples as blood plasma, serum or urine, the biochemical analyzer 60 causes a reagent taken from a reagent storage unit 61 and a sample taken from a sample storage unit 62 to react in a reaction vessel 63, and the calorimetric absorbance measurement apparatus 1 of the first embodiment measures the absorbance of a resultant reaction fluid to determine the cholesterol level, for instance, from obtained data.

The reagent storage unit 61 holds multiple reagent bottles 64 containing various reagents on a reagent tray and the sample storage unit 62 holds multiple sample tubes 65 containing blood plasma, serum or urine, for instance, on a sample tray. The biochemical analyzer 60 of this embodiment hold forty each reagent bottles 64 and sample tubes 65 on the respective trays. The reaction vessel 63 holds forty-five cuvettes 3 arranged in a circular form at regular intervals. The reagent storage unit 61, the sample storage unit 62 and the reaction vessel 63 individually rotate in a controlled fashion. The reagents and samples pipetted from the specified reagent bottles 64 and sample tubes 65 are injected into the individual cuvettes 3 through nozzles (not shown). The colorimetric absorbance measurement apparatus 1 measures the absorbance of a mixture (sample solution) of the reagent and sample in each cuvette 3 using the calorimetric absorbance measurement method.

As it is not possible to measure the absorbance of the sample solution in each cuvette 3 while moving the cuvettes 3 placed in the reaction vessel 63 in taking successive colorimetric absorbance measurements, it is necessary to alternately move and halt the cuvettes 3 to temporarily hold each successive cuvette 3 on the optical axis of a light beam emitted from a light source 2. The measurement is performed after vibrations caused by halting each cuvette 3 have completely ceased.

Operation of the calorimetric absorbance measurement apparatus 1 according to the first embodiment of the invention is described referring to FIG. 2. In the colorimetric absorbance measurement apparatus 1 of the embodiment, the light source 2 emits light and one of eight filters 11 of the filter assembly 10 placed on the optical axis of the light beam passes only such light components that have wavelengths falling within a range centering on a specific wavelength. The light components that have passed through the filter 11 further pass through the cuvette 3b containing a sample solution. The light attenuated after passing through the cuvette 3b is detected and converted into an electric signal through photoelectric conversion performed by a photosensor 6, for example. The electric signal is amplified by an amplifier (not shown), converted from analog form into digital form by an analog-to-digital (A/D) converter 7 and stored in a memory 9. Before the signal A/D-converted by the A/D converter 7 is stored in the memory 9, a timing generator circuit 8 transmits a memory command signal to the memory 9. Alternatively, data transmission may be performed in such a way that the signal A/D-converted by the A/D converter 7 is sent to the timing generator circuit 8 by serial communication, for instance, and the timing generator circuit 8 transmits the A/D-converted signal to the memory 9 together with a memory command signal.

The cuvettes 3a, 3b and 3c containing sample solutions are transferred to the position of the light beam in sequence such that they are successively placed and held on the optical axis of the light beam. In the example shown in FIG. 2, a colorimetric absorbance measurement is taken with the cuvette 3b which is currently held on the optical axis. Upon completion of the measurement, the cuvette 3c is transferred to the position of the light beam and held on the optical axis to take a next measurement. Measurements of the cuvettes 3a, 3b, 3c and so forth are sequentially taken while conveying and halting them in this fashion.

As an alternative, the circuit configuration of the calorimetric absorbance measurement apparatus 1 shown in FIG. 2 may be modified such that an electric current obtained by detecting and photoelectrically converting the light by the photosensor 6, for example, is output to a current-voltage amplifier (hereinafter referred to as an I/V amplifier) which converts a current into a voltage, and this voltage is output to and amplified by the aforementioned amplifier (not shown).

Also, the circuit configuration of the colorimetric absorbance measurement apparatus 1 may be constructed such that the timing generator circuit 8 transmits a signal to the aforementioned amplifier (not shown) and a voltage obtained through current-voltage conversion by an I/V amplifier is output to the A/D converter 7 after adjusting gain by the amplifier according to wavelengths needed for measurement.

Preferably, the light source 2 includes a lamp like a halogen lamp and a lens for converging the light emitted by the lamp and is associated with a fan for cooling the lamp.

As shown in FIG. 3, the filter assembly 10 has a circular filter disk 12 on which the aforementioned eight filters 11 are arranged in a circular pattern at regular intervals. There is formed a shaft hole 13 at the center of the filter disk 12. Each of filters 11 passes only such light components that have wavelengths falling within a range centering on a different specific wavelength.

To continuously rotate the filter disk 12 at a regular speed about its center, a shaft 20 is fitted in the shaft hole 13 and stepping motor 4 is joined to the filter disk 12 via the shaft 20 as shown in FIG. 2.

With this arrangement, the eight filters 11 are sequentially positioned on the optical axis, making it possible to take colorimetric absorbance measurements of light components of eight different wavelength ranges. Thus, the calorimetric absorbance measurement apparatus 1 of this embodiment has a capability to measure absorbances at eight different wavelengths. Typically, measurements are performed on two wavelengths using corresponding reagents in practice.

The stepping motor 4 for rotating the filter disk 12 is driven by a motor drive signal fed from a motor drive circuit 5. In this embodiment, the motor drive signal produced by the motor drive circuit 5 is transmitted to both the stepping motor 4 and the timing generator circuit 8 as shown in FIG. 2.

The timing generator circuit 8 detects the operation of the stepping motor 4 from the motor drive signal fed from the motor drive circuit 5. The timing generator circuit 8 transmits an A/D conversion start signal to the A/D converter 7 and the memory command signal to the memory 9 in synchronism with the timing at which the selected one of the eight filters 11 is positioned on the optical axis while the filter assembly 10 rotates, so that the signal output from the photosensor 6 is A/D-converted and stored in the memory 9. This arrangement ensures that measurements are taken with correct timing using the desired filters 11 even when the filter assembly 10 is continuously rotated at a fixed speed. When using only one filter 11, calorimetric absorbance measurements may be performed 16 times, for example, while the optical axis of the measuring light beam is passing through that filter 11.

The colorimetric absorbance measurement apparatus 21 according to the second embodiment of the invention is now described with reference to FIG. 4. This embodiment employs as an additional means for synchronizing the rotation of the filter assembly 10 with signal processing tasks an encoder 14 provided close to the stepping motor 4 for detecting its rotating speed. The timing generator circuit 8 controls signal processing means, such as the A/D converter 7, based on a rotating speed signal fed from the encoder 14.

As an alternative, the encoder 14 may be attached to the shaft 20 of the filter assembly 10 to detect its rotating speed and to control the signal processing means, such as the A/D converter 7, by the timing generator circuit 8. It is to be pointed out that the mounting site of the encoder 14 is not particularly limited as long as it enables synchronization of the rotation of the filter assembly 10 with the signal processing tasks.

The calorimetric absorbance measurement apparatus 31 according to the third embodiment of the invention is now described with reference to FIG. 5. This embodiment employs a motor/sensor control circuit 17 for synchronizing the rotation of the filter disk 12 with the rotation of the reaction vessel 63 containing a plurality of cuvettes such as 3a, 3b and 3c arranged in a circular form at regular intervals. The motor/sensor control circuit 17 transmits a motor driving command signal to the motor drive circuit 5. The motor drive circuit 5 transmits a motor drive signal from one output terminal thereof to both the stepping motor 15 and the timing generator circuit 8. The stepping motor 15 rotates the reaction vessel 63 through a shaft 16. Each of the cuvettes 3 held on the reaction vessel 63 is conveyed to the optical axis sequentially.

The timing generator circuit 8 detects the operation of the stepping motor 15 from the motor drive signal fed from the motor drive circuit 5. The timing generator circuit 8 transmits an A/D conversion start signal to the A/D converter 7 and a memory command signal to the memory 9 in synchronism with the timing at which the selected one of the eight filters 11 comes on the optical axis while the filter disk 12 rotates, so that a signal output from the photosensor 6 is A/D-converted and stored in the memory 9. This arrangement ensures that measurements are performed at correct timings using the desired filters 11 even when the filter disk 12 is continuously rotated at a fixed speed.

It should be appreciated from the foregoing discussion that, by causing the filter assembly 10 to continuously rotate at a regular speed as described above, the colorimetric absorbance measurement apparatus 1, 21 and 31 of the first, second and third embodiments solve the earlier-mentioned problem of the prior art that it is impossible to obtain measurements until vibrations caused by halting a light-dispersing device (filter assembly) cease, thereby enabling achievement of a high measuring efficiency. Furthermore, since the filter assembly 10 is rotated at the regular speed, the reliability of measurement data will not deteriorate due to the vibrations unlike the case of the prior art. Overall, the invention makes it possible to obtain highly reliable measurement data, shorten the period of time required for measurement and increases the number of wavelengths at which calorimetric absorbance measurements are performed within a given time period.

Figure 5:
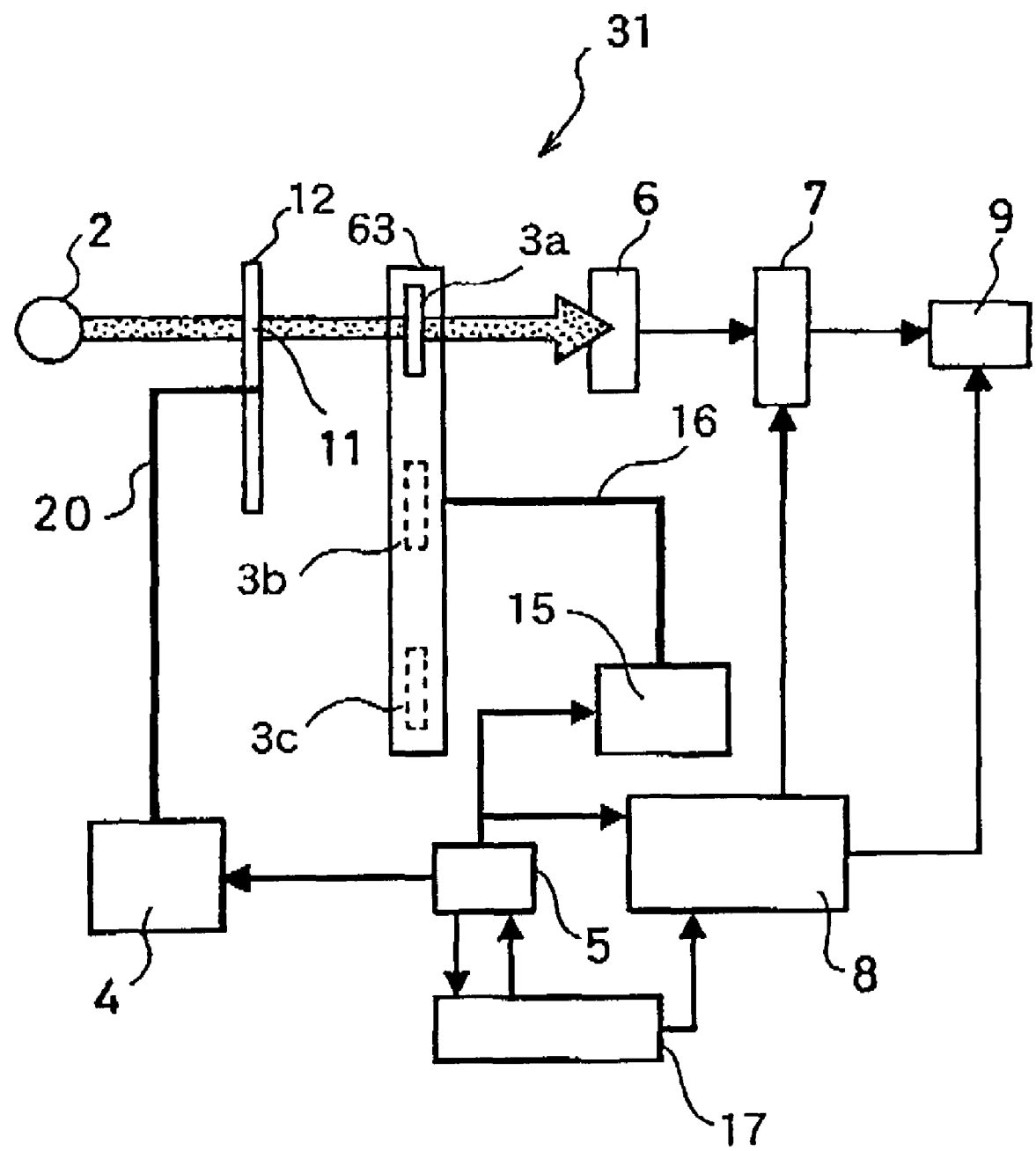
FIG. 5 is a block diagram of a calorimetric absorbance measurement apparatus according to a third embodiment of the invention.

When there are provided a plurality of cuvettes like the cuvettes 3a, 3b, 3c as shown in FIGS. 2, 4 and 5, it is necessary to transfer the cuvette 3c containing the sample solution to be measured next to the measuring position on the optical axis of the light beam upon completing the measurement of the preceding cuvette 3b. Since the colorimetric absorbance measurement apparatus 1, 21 of the invention provide a high measuring efficiency, a sufficient time period is allowed to wait until vibrations caused by halting each cuvette 3 completely fade away. It is therefore possible to prevent deterioration of measuring accuracy caused by the vibrations of the cuvettes 3. Furthermore, because measurements are successively taken with the multiple cuvettes 3a, 3b, 3c and so on, it is possible to obtain measurements of different samples one after another in a limited period of time.

It is to be understood that the invention is not limited to the aforementioned embodiments but is applicable in various forms and variations thereof as recited below, for example:

(1) While the filter assembly 10 is placed between the light source 2 and the cuvette 3b subjected to the measurement in the aforementioned embodiments, the filter assembly 10 may be placed between the cuvette 3b and the photosensor 6 so that light components of multiple wavelengths pass through the cuvette 3b subjected to the measurement and, then, only such light components that have wavelengths falling within a range centering on a specific wavelength pass through a selected one of the filters 11 and are detected by the photosensor 6.

(2) Although the filter assembly 10 carrying eight filters 11 is used in the embodiments, the number of filters 11 is not limited to eight, but any number of filters 11 may be arranged on the filter assembly 10.

(3) Synchronization between the rotation of the filter assembly 10 and the signal processing tasks may be accomplished by sending a signal output command to the photosensor 6 or by giving a signal processing command to a particular circuit element provided between the photosensor 6 and the memory 9.

(4) As an alternative arrangement for synchronizing the rotation of the filter assembly 10 with the signal processing tasks, the calorimetric absorbance measurement apparatus 1, 21 may be constructed such that the timing generator circuit 8 transmits a signal for controlling the operation of the stepping motor 4 to the motor drive circuit 5 and the timing generator circuit 8 controls signal processing means, such as the A/D converter 7, based on the motor drive signal delivered to the motor drive circuit 5.

What is claimed is:

1. A colorimetric absorbance measurement apparatus comprising:
   a light source which produces a measuring light beam along an optical axis;
   a plurality of cuvettes
      which are conveyed and halted such that the cuvettes intersect sequentially the optical axis of the measuring light beam produced by said light source,
      wherein at least one cuvette contains a sample and is conveyed to the optical axis of said measuring light beam during a measurement, and
      wherein said cuvettes are circularly disposed in a holder in a first plane, said first plane being substantially perpendicular to the optical axis of said measuring light beam;
   a first motor for conveying said cuvettes by rotating the cuvettes around a first axis which is substantially parallel to the optical axis of said measuring light beam, thereby causing each of said cuvettes to move to the optical axis of the measuring light beam sequentially;
   a filter assembly on which a plurality of filters are arranged in a circular pattern, each of the filters passing only such light components that have wavelengths falling within a wavelength range specific to said each of said filters, said wavelength range specific to said each of said filters having a center wavelength specific to said each of said filters;
   a second motor for rotating said filter assembly about its central axis which is substantially parallel to the optical axis of said measuring light beam, so as to rotate the filter assembly in a second plane which is substantially perpendicular to the optical axis of said measuring light beam, thereby causing the multiple filters to sequentially intersect the optical axis of said measuring light beam;
   a motor driver, said motor driver driving said second motor such that said filter assembly continuously rotates at a speed;
   a photoelectric converter performing photoelectric conversion in which light from said measuring light beam, which has passed through a selected one of the multiple filters when said filter assembly rotates at said speed and through said at least one cuvette, is converted into an electric signal;
   a signal processor for processing an output signal of the photoelectric converter for measuring absorbance of a fluid including said sample in said at least one cuvette; and a controller controlling said signal processor to perform the signal processing in synchronism with the timing at which the selected one of the multiple filters is positioned on the optical axis of the measuring light beam, wherein said controller synchronizes the signal processes with the rotation of said filter assembly based on a motor drive signal fed from said motor driver, and wherein during a measurement, one of said filters, one of said cuvettes, and said photoelectric converter are on the optical axis of the measuring light beam, and the cuvette which is on the optical axis of the measuring light beam is located between said filter assembly and said photoelectric converter along the optical axis of the measuring light beam.

2. The colorimetric absorbance measurement apparatus according to claim 1, wherein said controller transmits a control signal to said motor driver and synchronizes the signal processes with the rotation of said filter assembly based on said control signal.

3. The colorimetric absorbance measurement apparatus according to claim 1 further comprising:

an encoder operationally connected to said controller, said encoder outputting a rotating speed signal indicating the rotating speed of said second motor or said filter assembly;

wherein said controller synchronizes the signal processes with the rotation of said filter assembly based on the rotating speed signal fed from said encoder.

4. A colorimetric absorbance measurement apparatus comprising:

a light source which produces a measuring light beam along an optical axis;

a plurality of cuvettes containing samples, the cuvettes being conveyed to the optical axis of the measuring light beam produced by said light source, wherein said cuvettes are circularly disposed in a holder in a first plane, said first plane being substantially perpendicular to the optical axis of said measuring light beam;

a first motor for conveying said cuvettes by rotating the cuvettes around a first axis which is substantially parallel to the optical axis of said measuring light beam, thereby causing each of said cuvettes to move to the optical axis of the measuring light beam sequentially;

a filter assembly on which a plurality of filters are arranged in a circular pattern, each of the filters passing only such light components that have wavelengths falling within a wavelength range specific to said each of said filters, said wavelength range specific to said each of said filters having a center wavelength specific to said each of said filters;

a second motor, said motor continuously rotating said filter assembly about its central axis at a speed so as to rotate the filter assembly in a second plane which is substantially perpendicular to the optical axis of said measuring light beam, thereby causing the multiple filters to sequentially intersect the optical axis of the measuring light beam, wherein said central axis is substantially parallel to the optical axis of said measuring light beam;

a photoelectric converter for converting light from said measuring light beam, which has been emitted from said light source and passed through a selected one of the multiple filters when said filter assembly rotates at said speed and through the cuvettes on the optical axis of the measuring light beam, into an electric signal;

a signal processor for processing an output signal of said photoelectric converter for measuring absorbance of a fluid including one of said samples in one of said cuvettes; and a controller for synchronizing operation of said photoelectric converter with the timing at which the selected one of the multiple filters is positioned on the optical axis of the light beam, wherein during a measurement, one of said filters, one of said cuvettes, and said photoelectric converter are on the optical axis of the measuring light beam, and the cuvette which is on the optical axis of the measuring light beam is located between said filter assembly and said photoelectric converter along the optical axis of the measuring light beam.

5. A colorimetric absorbance measurement apparatus comprising:

a light source which produces a measuring light beam along an optical axis;

a plurality of cuvettes each containing a mixture of a reagent and a sample, said cuvettes being conveyed to the optical axis of the measuring light beam produced by said light source;

a reaction vessel on which the plurality of the cuvettes are arranged in a circular form at substantially regular intervals, wherein said reaction vessel rotates in a first plane which is substantially perpendicular to the optical axis of said measuring light beam;

a first motor for continuously rotating said reaction vessel around a first axis which is substantially parallel to the optical axis of said measuring light beam, thereby causing each of said multiple cuvettes held by the reaction vessel to move to said optical axis of the light beam sequentially;

a filter assembly on which a plurality of filters are arranged in a circular pattern, each of the filters passing only such light components that have wavelengths falling within a wavelength range specific to said each of said filters, said wavelength range specific to said each of said filters having a center wavelength specific to said each of said filters;

a second motor, said second motor continuously rotating said filter assembly about its central axis at a speed so as to rotate the filter assembly in a second plane which is substantially perpendicular to the optical axis of said measuring light beam, thereby causing the multiple filters to sequentially intersect the optical axis of the measuring light beam, wherein the central axis is substantially parallel to the optical axis of said measuring light beam;

a photoelectric converter for converting light from said measuring light beam, which has been emitted from said light source and passed through a selected one of the multiple filters when said filter assembly rotates at said speed and through one of the cuvettes on the optical axis of the light beam, into an electric signal;

a signal processor for processing an output signal of said photoelectric converter for measuring absorbance of the fluid contained in said one of the cuvettes; and a motor/sensor control circuit for synchronizing operation of said photoelectric converter with the timing at which the selected one of the multiple filters is on the optical axis of the measuring light beam, wherein during a measurement, one of said filters, one of said cuvettes, and said photoelectric converter are on the optical axis of the measuring light beam.

6. A colorimetric absorbance measurement apparatus comprising:
- a light source which produces a measuring light beam along an optical axis;
- a plurality of cuvettes conveyed by a reaction vessel;
- a first motor for continuously rotating said reaction vessel in a first plane, thereby causing the multiple cuvettes held by the reaction vessel to intersect sequentially the optical axis of the measuring light beam produced by said light source, wherein said first motor rotates said reaction vessel around a first axis which is substantially parallel to the optical axis of said measuring light beam;
- a filter assembly on which a plurality of filters are arranged;
- a second motor, said second motor rotating said filter assembly about its central axis at a speed so as to rotate the filter assembly in a second plane which is substantially perpendicular to the optical axis of said measuring light beam, thereby causing the multiple filters to sequentially intersect the optical axis of the measuring light beam, wherein said central axis is substantially parallel to the optical axis of said measuring light beam;
- a photoelectric converter for converting light from said measuring light beam, which has been emitted from said light source and passed through a selected one of the multiple filters when said filter assembly rotates at said speed and through one of the cuvettes on the optical axis of the measuring light beam, into an electric signal;
- a signal processor for processing an output signal of said photoelectric converter for measuring absorbance of a fluid in said one of the cuvettes; and
- a motor/sensor control circuit for synchronizing operation of said photoelectric converter with the timing at which the selected one of the multiple filters is on the optical axis of the measuring light beam,
- wherein during a measurement, one of said filters, one of said cuvettes, and said photoelectric converter are on the optical axis of the measuring light beam.

7. The colorimetric absorbance measurement apparatus according to claim 1, wherein
- said cuvettes are circularly disposed around said first axis to form a circle of a first radius in said first plane, and
- said filters are circularly disposed around said central axis to form a circle of a second radius in said second plane, wherein said second radius is smaller that said first radius.

8. The colorimetric absorbance measurement apparatus according to claim 4, wherein
- said cuvettes are circularly disposed around said first axis to form a circle of a first radius in said first plane, and
- said filters are circularly disposed around said central axis to form a circle of a second radius in said second plane, wherein said second radius is smaller that said first radius.

9. The colorimetric absorbance measurement apparatus according to claim 5, wherein
- said cuvettes are circularly disposed around said first axis to form a circle of a first radius in said first plane, and
- said filters are circularly disposed around said central axis to form a circle of a second radius in said second plane, wherein said second radius is smaller that said first radius.

10. The colorimetric absorbance measurement apparatus according to claim 5, wherein a cuvette which is on the optical axis of the measuring light beam during a measurement is located between said filter assembly and said photoelectric converter.

11. The colorimetric absorbance measurement apparatus according to claim 6, wherein
- said cuvettes are circularly disposed around said first axis to form a circle of a first radius in said first plane, and
- said filters are circularly disposed around said central axis to form a circle of a second radius in said second plane, wherein said second radius is smaller that said first radius.

12. The colorimetric absorbance measurement apparatus according to claim 6, wherein a cuvette which is on the optical axis of the measuring light beam during a measurement is located between said filter assembly and said photoelectric converter.

* * * * *